US008822659B2

(12) United States Patent
Lopez-Belmonte Encina et al.

(10) Patent No.: US 8,822,659 B2
(45) Date of Patent: Sep. 2, 2014

(54) PROCESS FOR THE SYNTHESIS OF UNPROTECTED PENTASACCHARIDES FROM A PROTECTED PENTASACCHARIDE PRECURSOR

(75) Inventors: Ivan Lopez-Belmonte Encina, Madrid (ES); Rafael Ojeda Martinez De Castilla, Madrid (ES)

(73) Assignee: Laboratorios Farmacéutios Rovi, S.A., Madrid (ES)

( * ) Notice: Subject to any disclaimer, the term of this patent is extended or adjusted under 35 U.S.C. 154(b) by 183 days.

(21) Appl. No.: 13/122,981

(22) PCT Filed: Oct. 2, 2009

(86) PCT No.: PCT/ES2009/070414
§ 371 (c)(1),
(2), (4) Date: Aug. 23, 2011

(87) PCT Pub. No.: WO2010/040880
PCT Pub. Date: Apr. 15, 2010

(65) Prior Publication Data
US 2011/0306757 A1    Dec. 15, 2011

(30) Foreign Application Priority Data
Oct. 8, 2008  (ES) .................. 200802855

(51) Int. Cl.
C08B 37/00   (2006.01)
C08B 37/10   (2006.01)
C07H 5/04    (2006.01)
C07H 5/06    (2006.01)
A61K 31/727  (2006.01)
C07H 15/04   (2006.01)
C07H 15/18   (2006.01)

(52) U.S. Cl.
CPC ............... *C07H 15/04* (2013.01); *C07H 15/18* (2013.01)

USPC .............................. 536/21; 536/55.3; 514/56

(58) Field of Classification Search
None
See application file for complete search history.

(56) References Cited

U.S. PATENT DOCUMENTS

| 4,841,041 A | 6/1989 | van Boeckel et al. |
| 7,541,445 B2 | 6/2009 | Seifert et al. |
| 2009/0187013 A1 | 7/2009 | Seifert et al. |

FOREIGN PATENT DOCUMENTS

| EP | 301618 | 2/1989 |
| WO | 03 022860 | 3/2003 |

OTHER PUBLICATIONS

Blaser et al. Journal of Molecular Catalysis A: Chemical 173 (2001) 3-18.*
de Paz et al. J. Am. Chem. Soc. 2006, 128, 2766-2767, including supporting information pp. S1-S14.*
Definition of Aryl Group, chemicool.com, downloaded from the internet Dec. 2013.*
Petitou, M., et al., "Synthesis of Heparinfragments: A Methyl α-Pentaoside with High Affinity for Antithrombin III," Carbohydrate Research, vol. 167, pp. 67-75, (1987).
International Search Report issued Jan. 14, 2010 in PCT/ES09/070414 filed Oct. 2, 2009.

* cited by examiner

*Primary Examiner* — Layla Bland
(74) *Attorney, Agent, or Firm* — Rick Matos; Innovar, L.L.C.

(57) ABSTRACT

Procedure for the synthesis of deprotected pentasaccharides from a protected precursor pentasaccharide through a reaction procedure having five stages whereamong is included an N-sulphation of amino groups and a hydrogenolysis of benzyl groups. Through this procedure a drastic reduction is achieved in the total synthesis time in comparison with the process traditionally employed, together with increased reproducibility thereof, permitting the standardization thereof.

22 Claims, No Drawings

PROCESS FOR THE SYNTHESIS OF UNPROTECTED PENTASACCHARIDES FROM A PROTECTED PENTASACCHARIDE PRECURSOR

FIELD OF THE INVENTION

The present invention refers to a new method for the synthesis of unprotected pentasaccharides from a protected pentasaccharide precursor.

INTRODUCTION

Heparins, highly-sulphated glycosaminoglycans, are compounds widely used as injectable anticoagulants. Heparins bind to the enzyme inhibitor, antithrombin (AT), causing a conformational change to it, resulting in its activation. Activated AT then deactivates thrombin and other proteases involved in blood coagulation, especially factor Xa. The speed of deactivation of these proteases by AT can be increased up to a factor of 1000 due to binding of heparin. Because of the formation of the ternary AT-thrombin-heparin complex, heparin activity against thrombin is dependent on its size. This has given rise to the development of low molecular weight heparins (LMWHs), one of which is fondaparinux. This is a synthetic pentasaccharide, with the chemical name O-(2-amino-2-deoxy-2-sulphamino-6-O-sulpho-α-D-glucopyranosyl)-(1→4)-O-(β-D-glucopyranosyl)-(1→4)-(2-amino-2-deoxy-2-sulphamino-3,6-di-O-sulpho-D-α-glucopyranosyl)-(1→4)-O-(2-O-sulpho-α-D-idopyranosyl)-(1→4)-methyl 2-amino-2-deoxy-2-sulphamino-6-O-sulpho-α-D-glucopyranoside as the decasodium salt, represented by the following chemical formula:

After a study of the current bibliography on the synthesis of this pentasaccharide and other related compounds, especially by the original groups (Petitou and Van Boeckel), it was found that the synthesis of these compounds has not changed much since the first synthetic procedures described in the early 1980s. The lack of change in 25 years gives a first idea of the complexity of the synthesis.

In the majority of patents and publications on the synthesis of this and other related oligosaccharides, a synthesis process is carried out in which, after a series of reaction steps that usually comprise stages of coupling lower oligosaccharides, a pentasaccharide precursor of fondaparinux is prepared with the following formula (Markush):

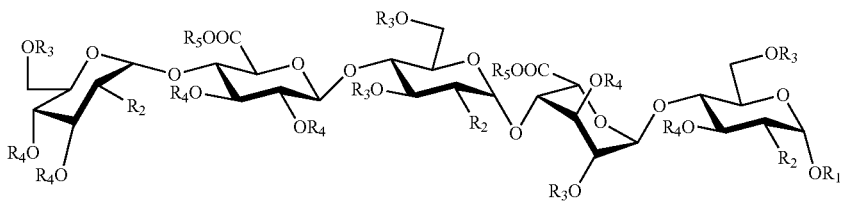

in which:

$R_1$ can be any branched, linear or cyclic alkyl group ($C_1$-$C_{20}$), for example methyl, ethyl, propyl, isopropyl, butyl, isobutyl, t-butyl, pentyl, benzyl or cyclohexyl;

$R_2$ can be azide or any amine protected by a carbamate group such as NH—Z, NH-Boc or NH-Troc;

$R_3$ can be any branched or linear aliphatic acyl group (for example acetyl, levulinoyl, etc.) or substituted or unsubstituted aromatic acyl (for example benzoyl, etc.);

$R_4$ can be any substituted or unsubstituted aryl group;

$R_5$ can be any branched, linear or cyclic alkyl group ($C_1$-$C_{20}$) or any substituted or unsubstituted aryl group.

In a preferred embodiment of the invention, $R_1$ is methyl, $R_2$ is azide or amine protected by a carbamate group such as NH—Z, $R_3$ is acetyl, $R_4$ is benzyl and $R_5$ is methyl, which gives rise to a compound of the following chemical formula, which represents the protected pentasaccharide precursor that is the preferred starting point of the process of the invention:

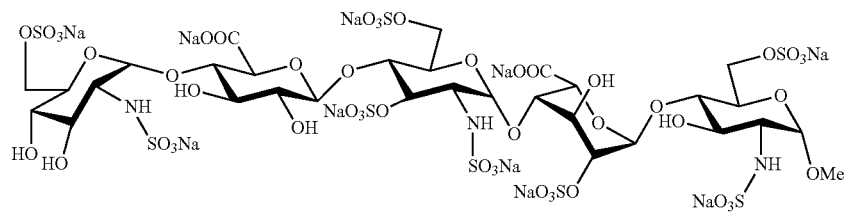

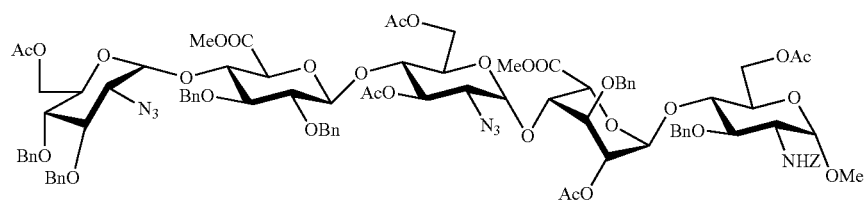

Starting from this compound, denominated "compound 38", it is necessary to perform some final deprotection/sulphatation stages in order to obtain fondaparinux. These stages, already known in the state of the art, can be listed as follows:
1. Saponification of the ester and methoxycarbonyl groups under strongly basic conditions.
2. O-sulphatation of the free hydroxyls generated in the previous stage.
3. Hydrogenolysis of the benzyl and azide groups.
4. N-sulphatation of the amines generated in the previous stage.

The sequence of this deprotection/sulphatation process known in prior art, starting from the preferred protected pentasaccharide precursor, is as follows:

Schema I (prior art)

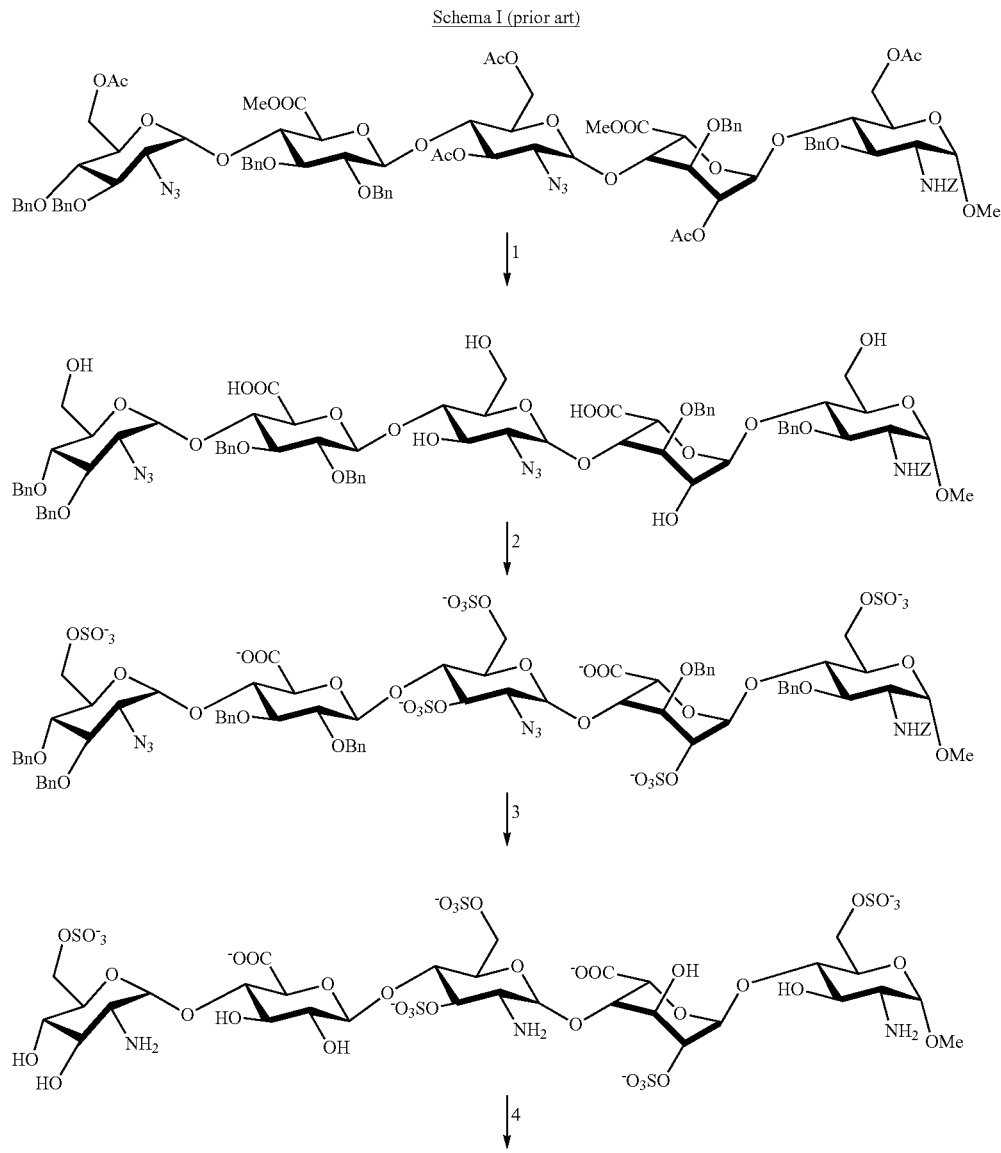

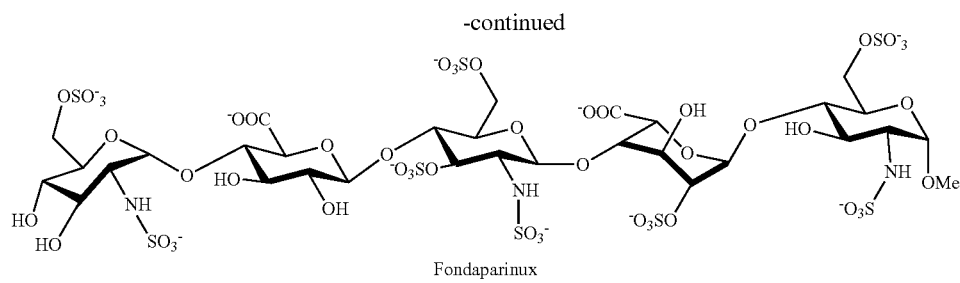

Fondaparinux

One of the key stages of this process is doubtless the simultaneous reduction of the benzyl and azide groups by hydrogenolysis (stage 3). The problems of reproducibility of this type of simultaneous reduction of both groups are well known, mainly not being able to control the speed of both reactions, where a major advance of one negatively interferes in the progress of the other. For this reason, it is difficult to establish a standard process that assures the termination of the reaction, with makes it necessary to monitor it continuously (e.g. via NMR, IR) to determine the termination of the reaction. This often leads to the need to stop the reaction and restart it again if the reaction has not finished. All of the above, linked to the fact that the reaction times are excessively long (2-6 days), encouraged the inventors to think about the possibility of optimising the process. Examples of all the above can be seen in: EP0347964A1; EP0301618A2; van Boeckel C. A. A., Petitou M., *Angew. Chem. Int. Ed. Engl.*, 1993, 32, 1671-1690; Petitou M., Jaury G., Derrien M., Choay J., *Bioorg. Med. Chem. Lett.*, 1991, 1, 95-98; Petitou M., Jacquinet J. C., Duchaussoy P., Lederman I., Choay J., Torri G., Sinay P., *Carbohydr. Res.*, 1986, 147, 221-236; Petitou M., Jacquinet J. C., Duchaussoy P., Lederman I., Choay J., Torri G., Sinay P., *Carbohydr. Res.*, 1987, 167, 67-75; Petitou M., Duchaussoy P., Lederman L., Choay J., Sinay P., *Carbohydr. Res.*, 1988, 179,163-172; Beetz T., van Boeckel C. A. A., *Tetrahedron Lett.*, 1986, 27, 5889-5892; Jacquinet J. C., Petitou M., Duchaussoy P., Lederman I., Choay J., Torri G., Sinay P., *Carbohydr. Res.*, 1984, 130, 221-241; Ichikawa Y., Monden R., Kuzuhara H., *Carbohydr. Res.*, 1988, 172, 37-64.

In the bibliography, a few cases where selective reduction of azides was carried out prior to hydrogenolysis of the benzyl groups were found (see, for example, the publication *Chem. Eur. J.* 2006, 12, 8664-8686; and also the international publication WO/2003/022860 of Alchemia Pty Ltd. et al). The sequence of reactions used in these cases were as follows:

1. Saponification of the ester and methoxycarbonyl groups.
2. O-sulphatation of the free hydroxyls generated in the previous stage.
3. Selective reduction of the azide groups.
4. N-sulphatation of the amines generated in the previous stage.
5. Hydrogenolysis of the benzyl groups.

Using this sequence of reactions leads, although with an extra step, to final products with shorter reaction times and with high process reproducibility. However, the application of this process to the case of this preferred protected pentasaccharide precursor does not give satisfactory results because the presence of a benzyloxycarbonyl group as a protector group of one of the amines does not allow total N-sulphatation. The sequence of reactions described gives rise to a new product and not to fondaparinux:

Schema II (prior art)

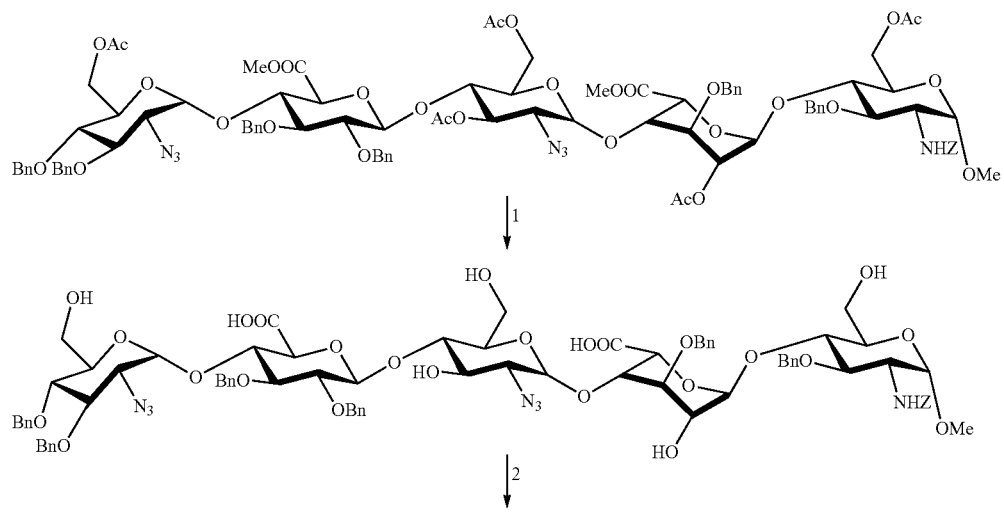

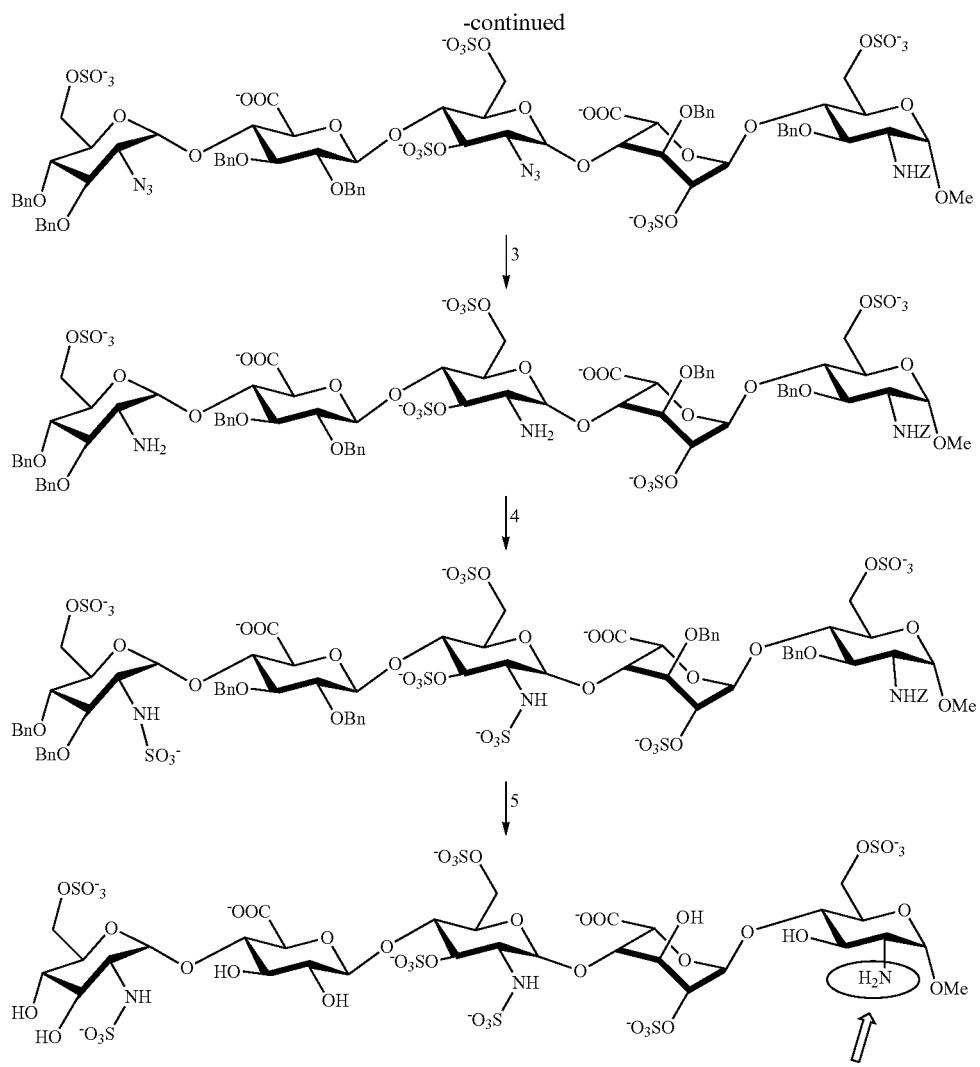

In this particular case, a last stage of sulphatation of the free amine is necessary.

Therefore, a process of deprotection/sulphatation would be useful that, starting from the preferred protected pentasaccharide precursor, would give rise to pentasaccharides such as fondaparinux with a faster global reaction time and better reproducibility than the processes described to date.

SUMMARY OF THE INVENTION

The problem resolved by the present invention is that of providing an alternative method for the synthesis of unprotected pentasaccharides that, starting from a protected pentasaccharide precursor, delivers pentasaccharides such as fondaparinux with a shorter processing time and higher reproducibility.

The solution is based on the inventors having found that, introducing an intermediate stage of selective reduction of the azide groups and inverting the order of the two following stages (the N-sulphatation of the amino groups and the hydrogenolysis of the benzyl groups), a dramatic reduction in total process time can be achieved. Simultaneous hydrogenolysis of the traditional process requires reaction times of between 2 and 6 days, whereas the stages of selective reduction of the azides and subsequent hydrogenolysis take 7 hours and 12 hours respectively. The reproducibility of the process is also such that it allows for standardisation, given that there is certainty that after the processes of 7 hours (selective reduction) and 12 hours (hydrogenolysis) under the conditions indicated, the desired final product is obtained. This is not always so in the case of total reduction.

An expert in the art will not find this solution obvious because while the process commonly used in the state of the art for the preparation of fondaparinux is that shown in Schema I, which is the process most widely used in the state of the art and which is known to work, although with the limitations previously indicated, it will therefore be the process chosen by the expert to prepare fondaparinux. A modification of this process which involves inverting the order of two of the reaction stages plus introducing a third stage, such as that proposed in the present invention, would not be considered at all from any point of view to be an obvious variant of the known process.

In this way, a first aspect of the invention is a method for producing unprotected pentasaccharides, including fondaparinux, starting from a protected precursor of the formula:

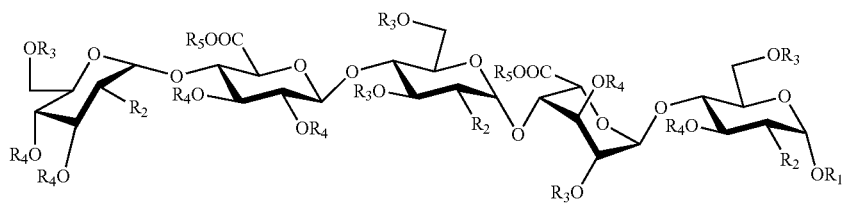

in which:

- $R_1$ can be any branched, linear or cyclic alkyl group ($C_1$-$C_{20}$), for example methyl, ethyl, propyl, isopropyl, butyl, isobutyl, tert-butyl, pentyl, benzyl or cyclohexyl;
- $R_2$ can be azide or any amine protected by a carbamate group such as NH—Z, NH-Boc or NH-Troc, in which at least one of the $R_2$ must be an azide and at least one of the $R_2$ must be an NH—Z;
- $R_3$ can be any branched or linear aliphatic acyl group (for example acetyl, levulinoyl, etc.) or substituted or unsubstituted aromatic acyl (for example benzoyl, etc.);
- $R_4$ can be any substituted or unsubstituted aryl group;
- $R_5$ can be any branched, linear or cyclic alkyl group ($C_1$-$C_{20}$) or any substituted or unsubstituted aryl group.

The process of the invention comprises the following stages:

1. Saponification of the ester and methoxycarbonyl groups under strongly basic conditions.
2. O-sulphatation of the free hydroxyls generated in the previous stage.
3. Selective reduction of the azide groups.
4. Hydrogenolysis of the benzyl groups.
5. N-sulphatation of the amines generated in stages 3 and 4.

This sequence of this process is as follows:

Schema III

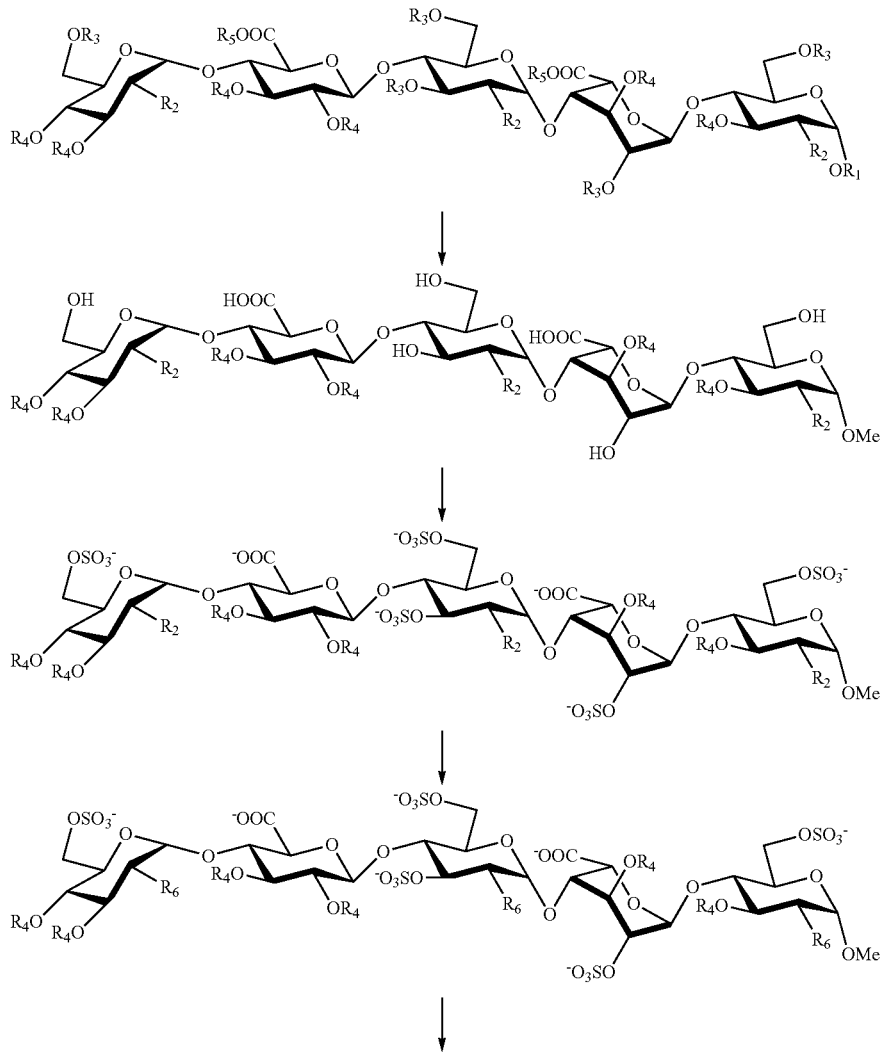

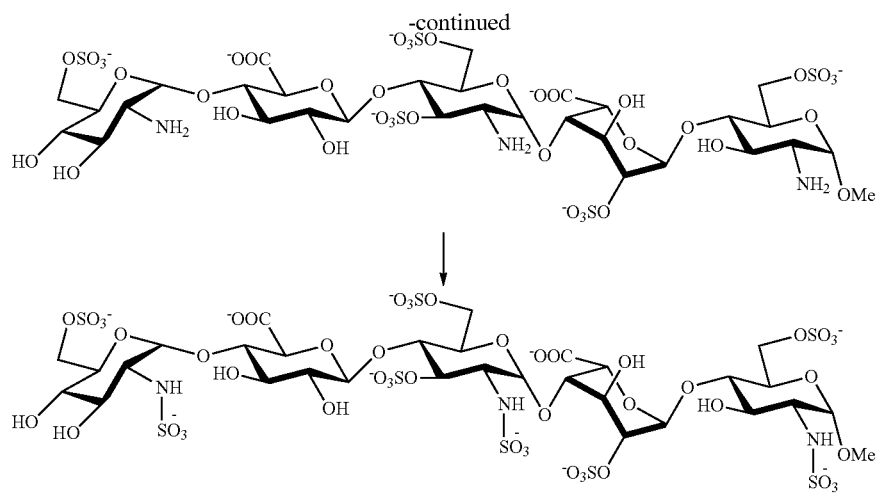

in which:
- $R_1$ can be any branched, linear or cyclic alkyl group ($C_1$-$C_{20}$), for example methyl, ethyl, propyl, isopropyl, butyl, isobutyl, tert-butyl, pentyl, benzyl or cyclohexyl;
- $R_2$ can be azide or any amine protected by a carbamate group such as NH—Z, NH-Boc or NH-Trot, in which at least one of the $R_2$ must be an azide and at least one of the $R_2$ must be a NH—Z;
- $R_3$ can be any branched or linear aliphatic acyl group (for example acetyl, levulinoyl, etc.) or substituted or unsubstituted aromatic acyl (for example benzoyl, etc.);
- $R_4$ can be any substituted or unsubstituted aryl group;
- $R_5$ can be any branched, linear or cyclic alkyl group ($C_1$-$C_{20}$) or any substituted or unsubstituted aryl group;
- $R_6$ can be NH, or NH—Z, with at least one of them being NH—Z.

The specific case in which the starting material is the preferred protected pentasaccharide precursor (Compound 38), the specific schema is as follows:

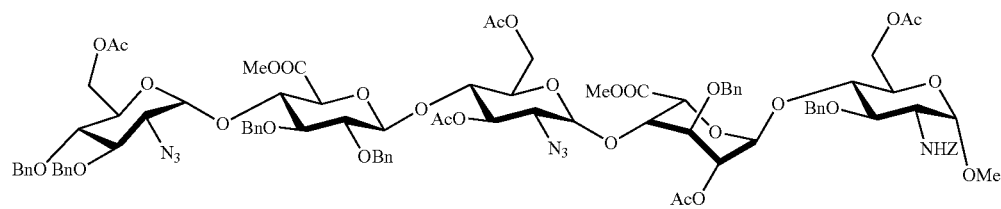

38

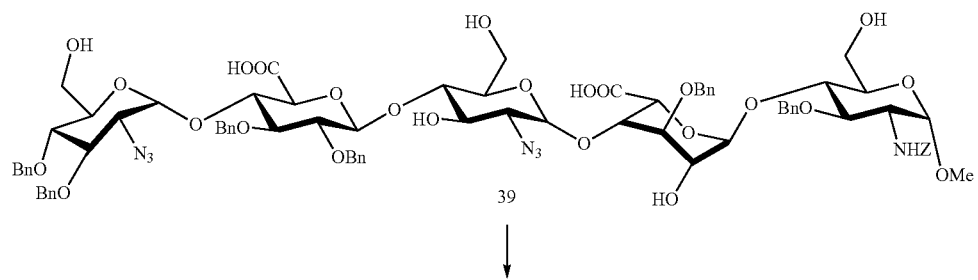

39

-continued

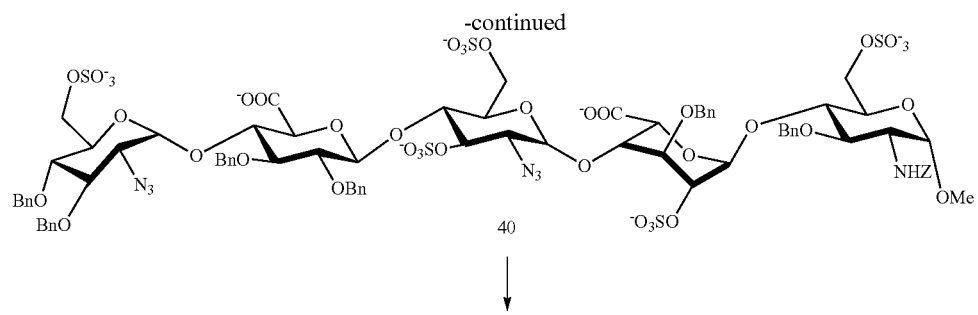

40

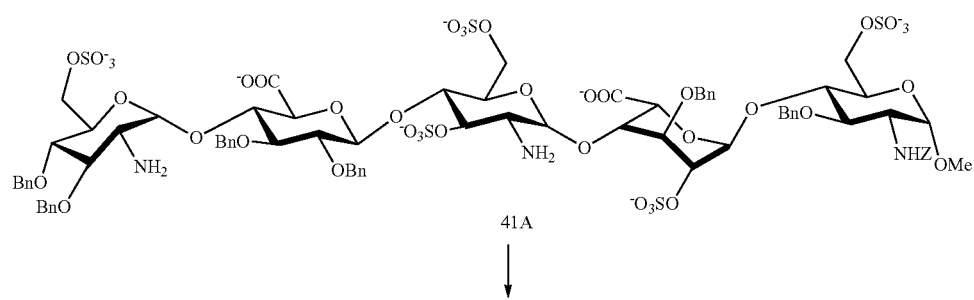

41A

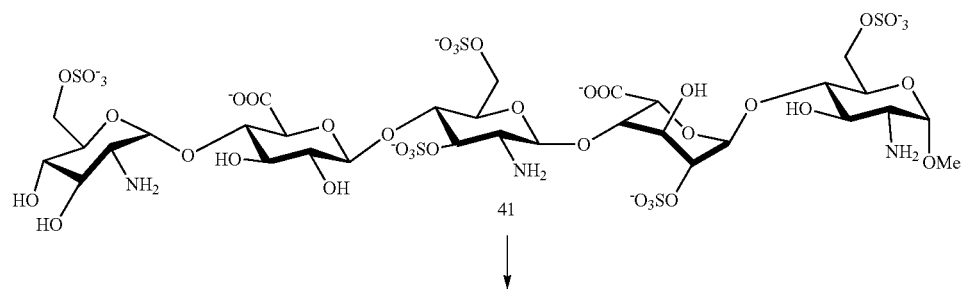

41

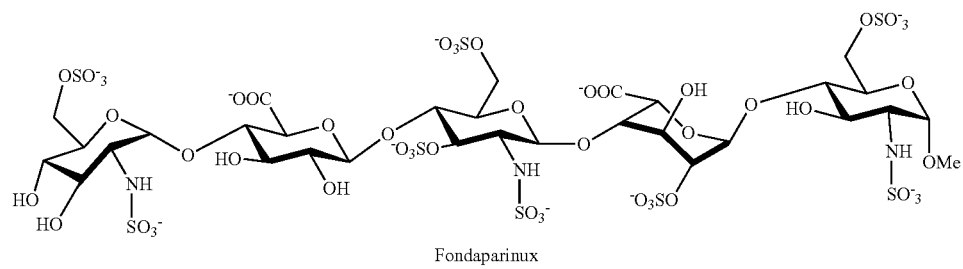

Fondaparinux

This sequence of reactions has been carried out successfully with the protected pentasaccharide precursor and fondaparinux was obtained with purity similar to that of the earlier processes described, but essentially in less time and with total reproducibility in the various trials that were carried out.

Lastly, it should be mentioned that the change in the order of these two reactions provides additional advantages from the practical point of view, because in this case, the N-sulphatation is carried out in aqueous medium, without control of pH or the need for an inert atmosphere or dry solvents, which doubtless simplifies the processes greatly.

DETAILED DESCRIPTION OF THE INVENTION

The embodiment of the process of synthesis of pentasaccharides developed by the inventors is described below:

(1) Saponification

O-(2-azido-3,4-di-O-benzyl-2-deoxy-α-D-glucopy-
ranosyl)-(1→4)-O-(2,3-di-O-benzyl-β-D-glucopyra-
nosyl)-(1→4)-(2-azido-2-deoxy-D-α-glucopyrano-
syl)-(1→4)-O-(3-O-benzyl-α-D-idopyranosyl)-
(1→4)-methyl 3-O-benzyl-2-N-benzyloxicarbonyl-
2-deoxy-α-D-glucopyranoside (39)

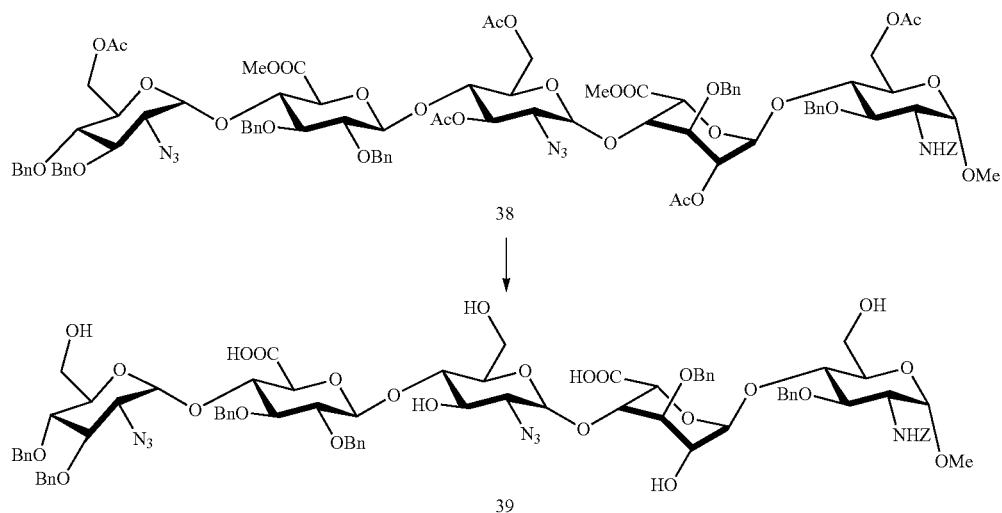

To a solution of compound 38 (266 mg, 145 µmol) in THF (10 ml) at 0° C., 30% H₂O (5.8 ml) and an aqueous solution of 0.7 M LiOH (3.5 ml) were added. After stirring for 16 hours at room temperature, MeOH (10 ml) and an aqueous solution of 4 M NaOH (3.8 ml) were added. After another 24 hours, the reaction was neutralised with 6M HCl. The reaction mixture was diluted with H₂O and the aqueous phase extracted with CH₂Cl₂. The organic phase was washed with 10% Na₂SO₃ and with H₂O, dried and concentrated to obtain compound 39 (200 mg, 89%).

(2) O-Sulphatation

O-(2-azido-3,4-di-O-benzyl-2-deoxy-6-O-sulpho-α-
D-glucopyranosyl)-(1→4)-O-(2,3-di-O-benzyl-(3-D-
glucopyranosyl)-(1→4)-(2-azido-2-deoxy-3,6-di-O-
sulpho-D-α-glucopyranosyl)-(1→4)-O-(3-O-benzyl-
2-O-sulpho-α-D-idopyranosyl)-(1→4)-methyl 3-O-
benzyl-benzyloxycarbonyl-2-deoxy-6-O-sulpho-α-
D-glucopyranoside (40 as the heptasodium salt)

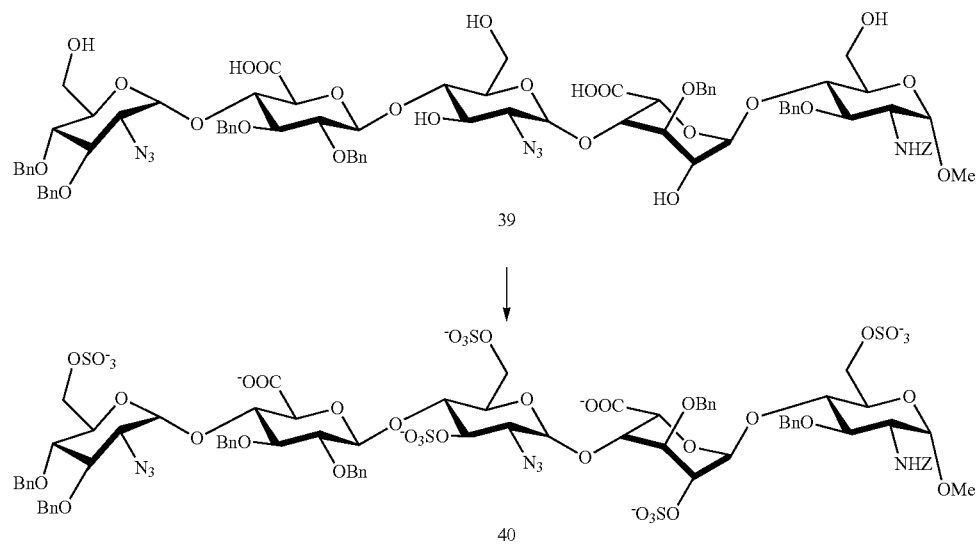

A suspension of compound 39 (200 mg, 125 μmol) and sulphur trioxide-trimethylamine complex (220 mg, 0.157 mmol) in N,N-dimethylformamide (10 ml) was stirred at 60° C. for 24 hours. The mixture was cooled and methanol (8 ml) and dichloromethane (8 ml) were added. The solution was passed through a Sephadex LH-20 column in methanol/dichloromethane (1:1), and then through an ion exchange column (Dowex 50WX4-Na$^+$) to give compound 40 (228 mg, 85%).

(3) Selective Reduction of Azide Groups

O-(2-amino-3,4-di-O-benzyl-2-deoxy-6-O-sulpho-α-D-glucopyranosyl)-(1→4)-O-(2,3-di-O-benzyl-β-D-glucopyranosyl)-(1→4)-(2-amino-2-deoxy-3,6-di-O-sulpho-D-α-glucopyranosyl)-(1→4)-O-(3-O-benzyl-2-O-sulpho-α-D-idopyranosyl)-(1→4)-methyl 3-O-benzyl-2-N-benzyloxycarbonyl-2-deoxy-6-O-sulpho-α-D-glucopyranoside (41A as the heptasodium salt)

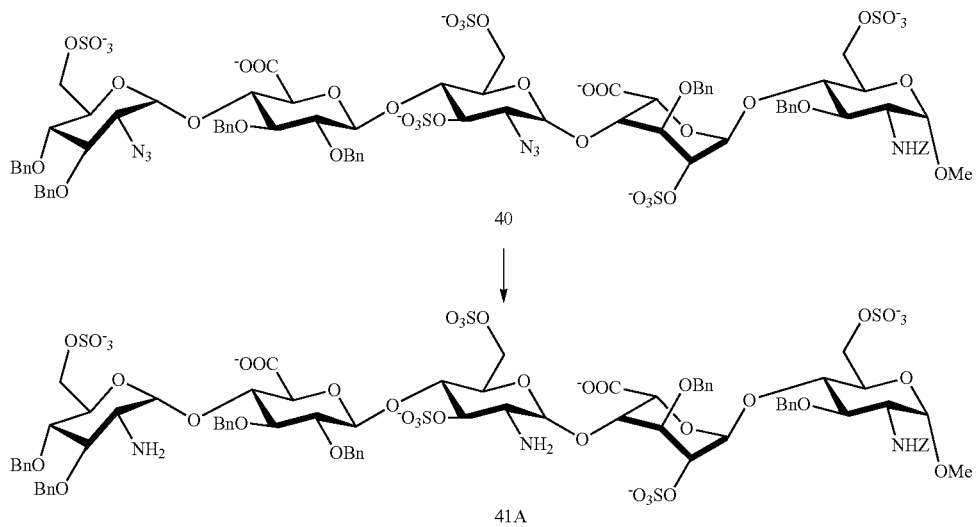

Compound 40 (228 mg, 106 mmol$_{[P1]}$) dissolved in THF (32 ml) was treated with an aqueous solution of 0.1M NaOH (33 ml). Next, a solution of 1M PMe3 in THF (4.5 ml) was added and the reaction stirred for 8 hours. The reaction mixture was neutralised with an aqueous solution of 0.1M HCl, concentrated and purified on Sephadex LH-20 in methanol/dichloromethane (1:1) to produce compound 41A (205 mg, 92%).

(4) Hydrogenolysis

O-(2-amino-2-deoxy-6-O-sulpho-α-D-glucopyranosyl)-(1→4)-O-(β-D-glucopyranosyl)-(1→4)-(2-amino-2-deoxy-3,6-di-O-sulpho-D-α-glucopyranosyl)-(1→4)-O-(2-O-sulpho-α-D-idopyranosyl)-(1→4)-methyl 2-amino-2-deoxy-6-O-sulpho-α-D-glucopyranoside (41 as the heptasodium salt)

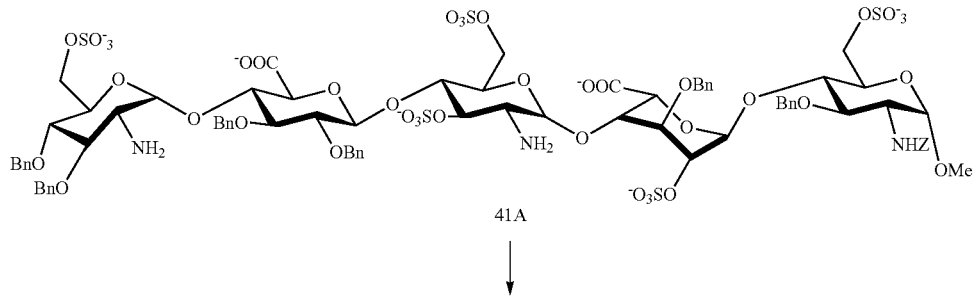

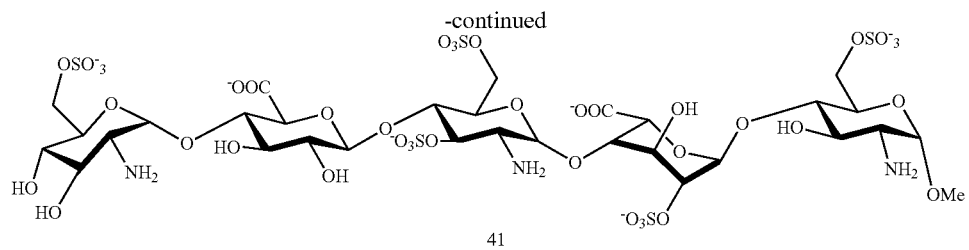

41

Compound 40 (205 mg, 98 mmol$_{[p2]}$) in methanol-H$_2$O (12 ml, 3:1) was hydrogenated in the presence of Pd(OH)$_2$ on Carbon (20 wt. % Pd) (300 mg). The reaction mixture was filtered after 8 hours of stirring. The filtrate was concentrated and the reaction crude was used in the next stage without any additional purification.

(5) N-Sulphatation

O-(2-amino-2-deoxy-2-sulphamino-6-O-sulpho-α-D-glucopyranosyl)-(1→4)-O-(β-D-glucopyranosyl)-(1→4)-(2-amino-2-deoxy-2-sulphamino-3,6-di-O-sulpho-D-α-glucopyranosyl)-(1→4)-O-(2-O-sulpho-α-D-idopyranosyl)-(1→4)-methyl 2-amino-2-deoxy-2-sulphamino-6-O-sulpho-α-D-glucopyranoside as the decasodium salt (fondaparinux)

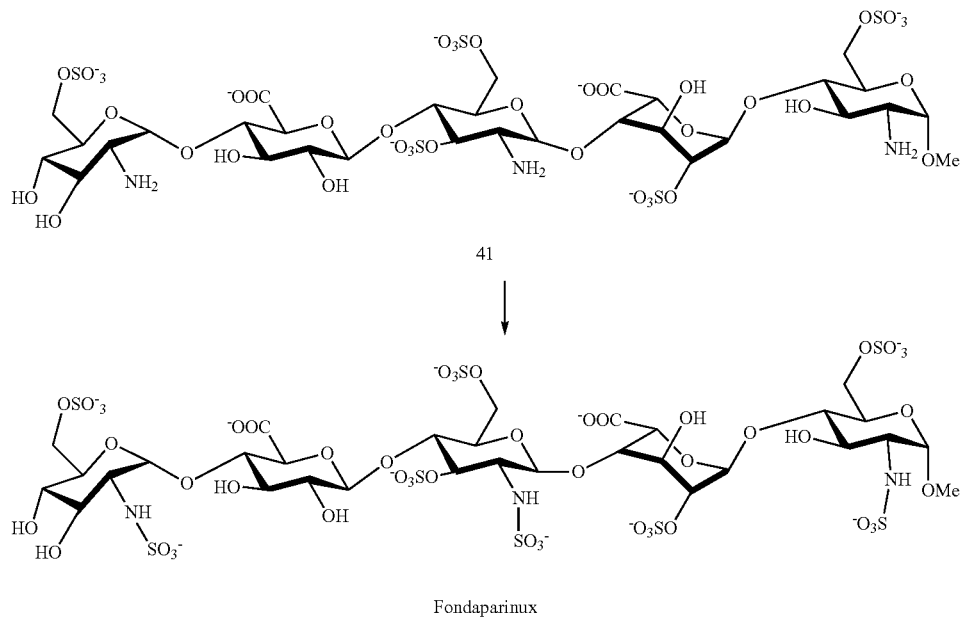

Fondaparinux

To a crude solution of the above compound in H$_2$O (12 ml), Na$_2$CO$_3$ (100 mg) and the sulphur trioxide-pyridine complex (100 mg) were added. A second, third and fourth addition of Na$_2$CO$_3$ (100 mg) and sulphur trioxide-pyridine complex (100 mg) were carried out at 2, 4 and 6 hours. At 16 hours, the reaction mixture was purified on Sephadex G-25 in H$_2$O/MeOH (9:1). The fractions containing the product were combined and concentrated to dryness. Finally, the residue was passed through a Dowex 50WX4-Na column. The fractions containing the product were combined and lyophilised to produce fondaparinux (115 mg, 68% from compound 41).

In summary, the advantages of this process of 5 stages compared to the conventional process of 4 stages or even the original 5-stage process are listed below:

1. Dramatic reduction in the total time required for the process as simultaneous hydrogenolysis requires reaction times of between 2 and 6 days, whereas the selective reduction of azides and then the subsequent hydrogenolysis stages take 7 hours and 12 hours respectively.
2. Reproducibility of the process, which enables its standardisation. Under the conditions indicated, there is certainty that after the selective reduction and the hydrogenolysis processes the final product is obtained without any need for an intermediate check to confirm the termination of the various reactions, which is not always the case with total reduction.
3. Compared to the previous 5-stage N-sulphatation process before hydrogenolysis, which required dry conditions and high quality solvents, the present proposed process does not require such conditions (being performed in aqueous medium).

The invention claimed is:

1. A method of preparation of at least one pentasaccharide starting from a protected precursor of the formula (1):

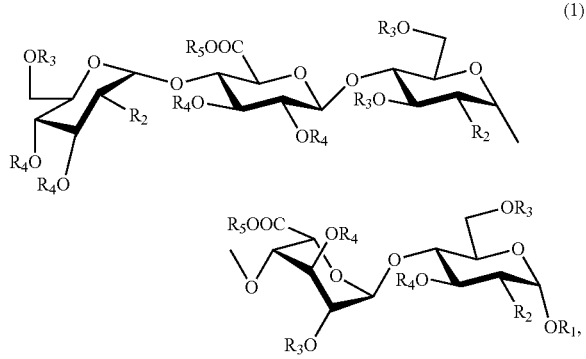

(1)

wherein:
- $R_1$ is a branched, linear, or cyclic alkyl group ($C_1$-$C_{20}$);
- $R_2$ is independently azide or an amine protected by a carbamate group, in which at least one of the $R_2$ is an azide and at least one of the $R_2$ is an amine protected by a carbamate group;
- $R_3$ is a branched or linear aliphatic acyl group or a substituted or unsubstituted aromatic acyl;
- $R_4$ is a substituted or unsubstituted benzyl group;
- $R_5$ is a branched, linear, or cyclic alkyl group ($C_1$-$C_{20}$) or any substituted or unsubstituted aryl group;

the process comprising, in order:
i) saponifying the ester and methoxycarbonyl groups of the protected precursor compound by reacting the precursor compound with concentrated NaOH, giving rise to a compound of formula (2):

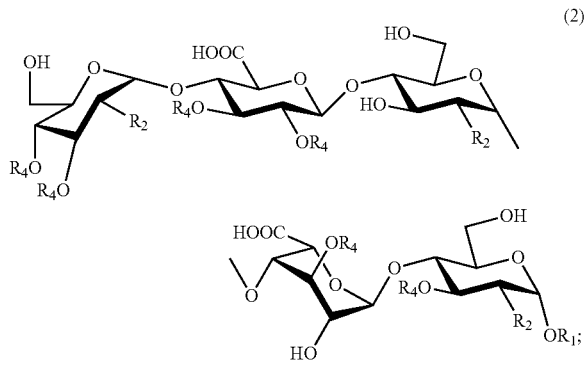

(2)

ii) O-sulfating free hydroxyls of the compound of formula (2) by reacting the compound of formula (2) with sulphur trioxide-trimethylamine complex, giving rise to a compound of formula (3):

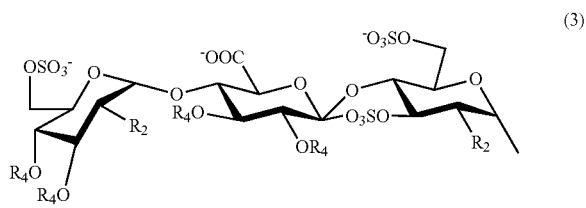

(3)

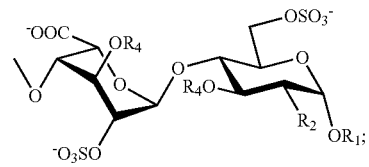

iii) selectively reducing the azide groups of the compound of formula (3) by reacting the compound of formula (3) with $P(CH_3)_3$, giving rise to a compound of formula (4):

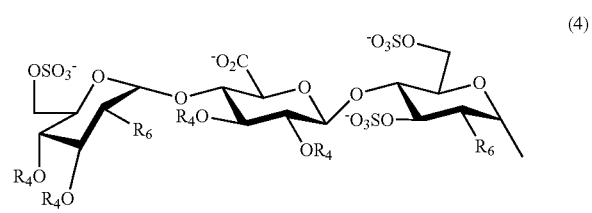

(4)

wherein $R_6$ is independently $NH_2$ or an amine protected by a carbamate group, and at least one $R_6$ is an amine protected by a carbamate group;

iv) hydrogenating benzyl groups of the compound of formula (4) by reacting the compound of formula (4) in the presence of hydrogen with $Pd(OH)_2$ on carbon/20% by weight of Pd, giving rise to a compound of formula (5):

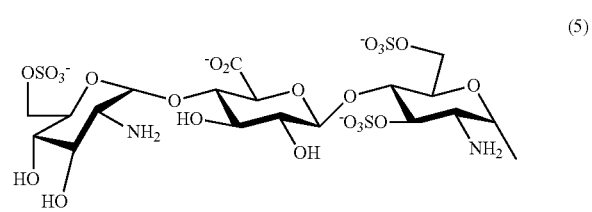

(5)

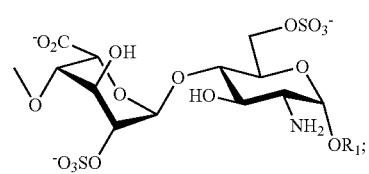

v) N-sulfating amines of the compound of formula (5) by reacting the compound of formula (5) with sulphur trioxide-pyridine complex, giving rise to a compound of formula (6):

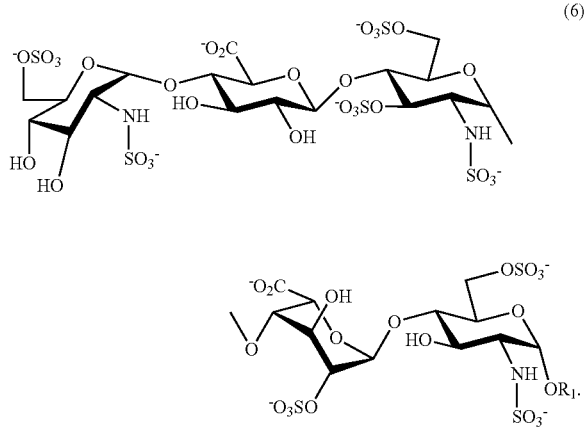

(6)

2. The method of claim 1, wherein
$R_1$ is methyl,
$R_2$ is an amine protected by a carbamate group or $N_3$, with at least one of the $R_2$ being an amine protected by a carbamate group and at least one of the $R_2$ being a $N_3$,
$R_3$ is acetyl,
$R_4$ is benzyl,
$R_5$ is methyl, and
$R_6$ is $NH_2$ or an amine protected by a carbamate group, with at least one of $R_6$ being an amine protected by a carbamate group.

3. The method of claim 1, wherein the saponifying (i) is carried out in THF medium at 0° C., with addition of $H_2O_2$ to 30% w/w and an aqueous solution of LiOH.

4. The method of claim 1, wherein the O-sulfating (ii) is carried out in N,N-dimethylformamide with stifling at a temperature of 60° C. for 24 hours.

5. The method of claim 1, wherein the selectively reducing (iii) is carried out in THF in basic medium.

6. The method of claim 1, wherein the hydrogenating (iv) is carried out in methanol-$H_2O$ medium.

7. The method of claim 1, wherein the N-sulfating (v) is carried out in aqueous medium with the addition of $Na_2CO_3$.

8. The method of claim 1, wherein further comprising, after the N-sulfating (v):
purifying a product obtained, comprising the compound of formula (6), by molecular exclusion chromatography in at least one hydro-alcoholic mixture, to give a second product.

9. The method of claim 8, further comprising:
subjecting the second product to ion exchange to obtain a sodium salt of the at least one pentasaccharide.

10. The method of claim 1, wherein, in the protected precursor of the formula (1),
$R_3$ is acetyl or levulinoyl or benzoyl.

11. The method of claim 2, wherein the saponifying (i) is carried out in THF medium at 0° C., with addition of $H_2O_2$ to 30% and an aqueous solution of LiOH.

12. The method of claim 2, wherein the O-sulfating (ii) is carried out in N,N-dimethylformamide with stifling at a temperature of 60° C. for 24 hours.

13. The method of claim 3, wherein the O-sulfating (ii) is carried out in N,N-dimethylformamide with stifling at a temperature of 60° C. for 24 hours.

14. The method of claim 2, wherein the selectively reducing (iii) is carried out in THF in basic medium.

15. The method of claim 3, wherein the selectively reducing (iii) is carried out in THF in basic medium.

16. The method of claim 4, wherein the selectively reducing (iii) is carried out in THF in basic medium.

17. A method of preparation of at least one pentasaccharide starting from a protected precursor of the formula (1):

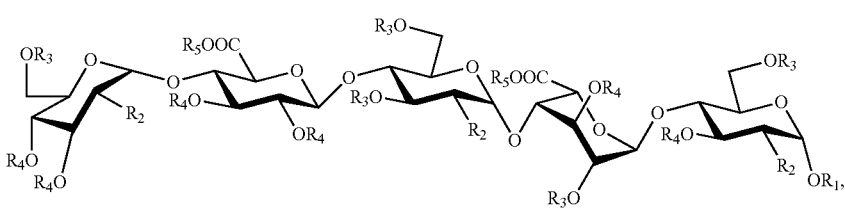

(1)

wherein:

$R_1$ is a branched, linear, or cyclic alkyl group ($C_1$-$C_{20}$);
$R_2$ is independently azide or an amine protected by a carbamate group, in which at least one of the $R_2$ is an azide and at least one of the $R_2$ is an amine protected by a carbamate group;
$R_3$ is a branched or linear aliphatic acyl group or a substituted or unsubstituted aromatic acyl;
$R_4$ is a substituted or unsubstituted benzyl group;
$R_5$ is a branched, linear, or cyclic alkyl group ($C_1$-$C_{20}$) or any substituted or unsubstituted aryl group;

the process comprising, in order:
i) saponifying the ester and methoxycarbonyl groups of the protected precursor compound to form a compound of formula (2):

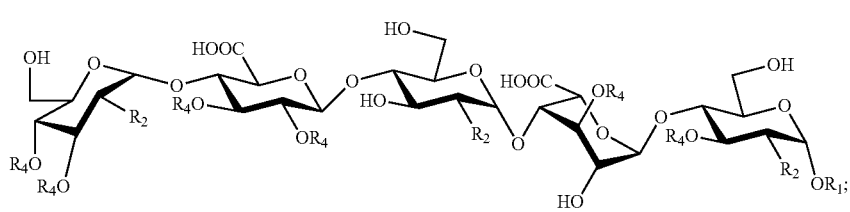

(2)

ii) O-sulfating free hydroxyls of the compound of formula (2) to form a compound of formula (3):

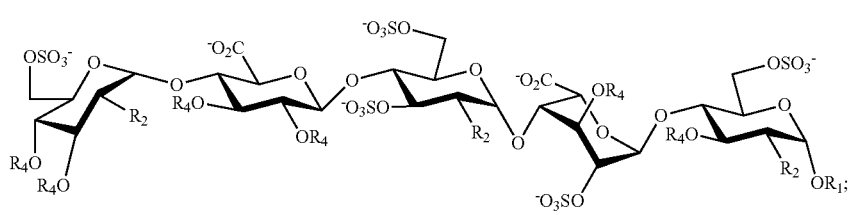

(3)

iii) selectively reducing the azide groups of the compound of formula (3) to form a compound of formula (4):

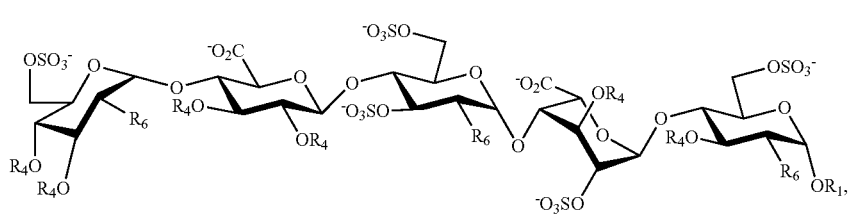

(4)

wherein $R_6$ is independently $NH_2$ or an amine protected by a carbamate group, and at least one $R_6$ is an amine protected by a carbamate group;

iv) hydrogenating benzylic groups of the compound of formula (4) to form a compound of formula (5):

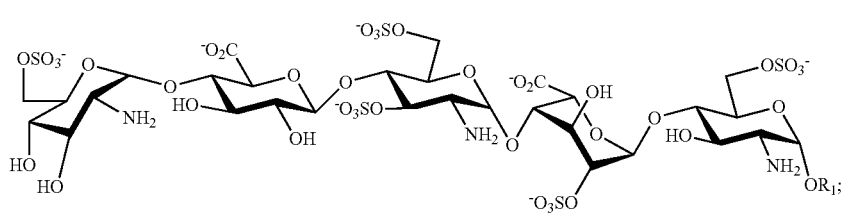

(5)

v) N-sulfating amines of the compound of formula (5) to form a compound of formula (6):

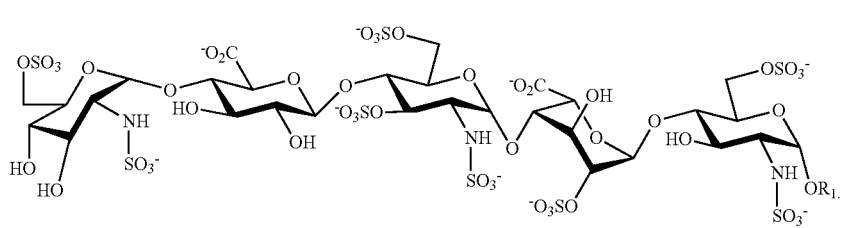

(6)

18. The method of claim 17, wherein, in the protected precursor of the formula (1), $R_1$ is methyl, ethyl, propyl, isopropyl, butyl, isobutyl, tert-butyl, pentyl, or cyclohexyl.

19. The method of claim 18, wherein, in the protected precursor of the formula (1), $R_2$ is an amine protected by a carbamate group or $N_3$, with at least one of the $R_2$ being an amine protected by a carbamate group and at least one of the $R_2$ being a $N_3$, $R_3$ is acetyl, $R_4$ is benzyl, $R_5$ is methyl, and at least one of $R_6$ being an amine protected by a carbamate group.

20. The method of claim 19, wherein
the saponifying is conducted with concentrated NaOH;
the O-sulfating is conducted with sulphur trioxide-trimethylamine complex;
the selectively reducing is conducted with $P(CH_3)_3$;
the hydrogenating is conducted in the presence of hydrogen with $Pd(OH)_2$ on carbon/20% by weight of Pd; and
the N-sulfating is conducted with sulphur trioxide-pyridine complex.

21. The compound of formula (4)

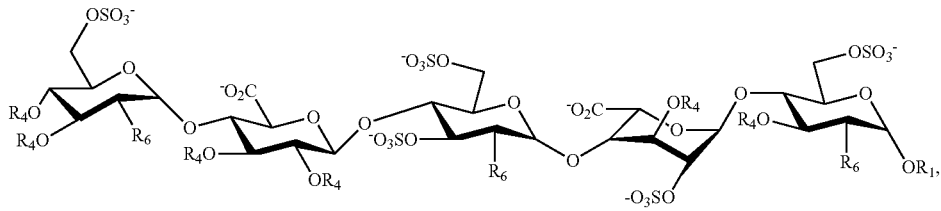

(4)

wherein
$R_1$ is a branched, linear, or cyclic alkyl group ($C_1$-$C_{20}$);
$R_4$ is independently substituted or unsubstituted aryl group; and
$R_6$ is independently $NH_2$ or an amine protected by a carbamate group, and at least one $R_6$ is an amine protected by a carbamate group.

22. A method of preparation of at least one pentasaccharide starting from a protected precursor of the formula (1):

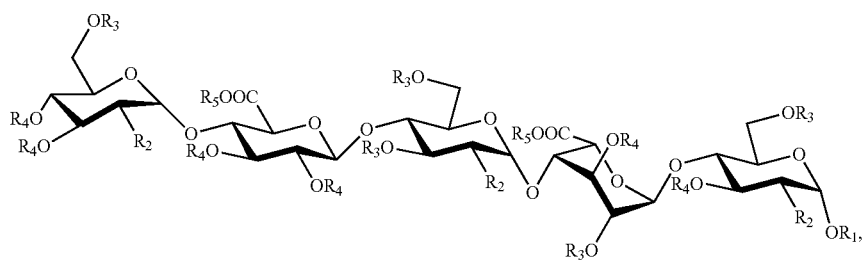

(1)

wherein:
$R_1$ is a branched, linear, or cyclic alkyl group ($C_1$-$C_{20}$);
$R_2$ is independently azide or an amine protected by a carbamate group, in which at least one of the $R_2$ is an azide and at least one of the $R_2$ is an amine protected by a carbamate group;
$R_3$ is a branched or linear aliphatic acyl group or a substituted or unsubstituted aromatic acyl;
$R_4$ is a substituted or unsubstituted aryl group;
$R_5$ is a branched, linear, or cyclic alkyl group ($C_1$-$C_{20}$) or any substituted or unsubstituted aryl group;
the process comprising, in order:
i) reacting the precursor compound of Formula (1) with concentrated NaOH, giving rise to a compound of formula (2):

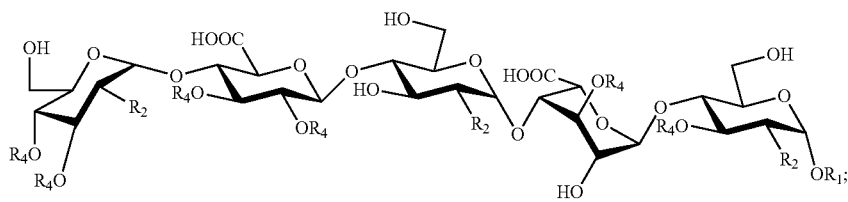

(2)

ii) reacting the compound of Formula (2) with sulphur trioxide-trimethylamine complex, giving rise to a compound of Formula (3):

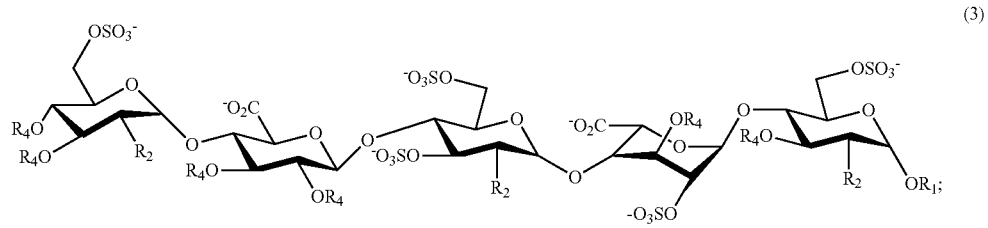

iii) reacting the compound of Formula (3) with P(CH$_3$)$_3$, giving rise to a compound of formula (4):

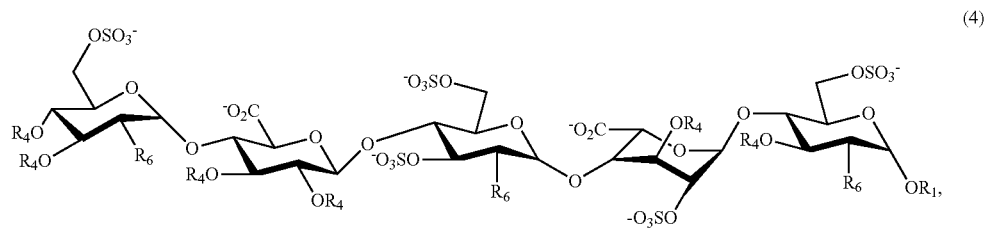

wherein R$_6$ is independently NH$_2$ or an amine protected by a carbamate group, and at least one R$_6$ is an amine protected by a carbamate group;

iv) reacting the compound of Formula (4) in the presence of hydrogen with Pd(OH)$_2$ on carbon/20% by weight of Pd, giving rise to a compound of formula (5):

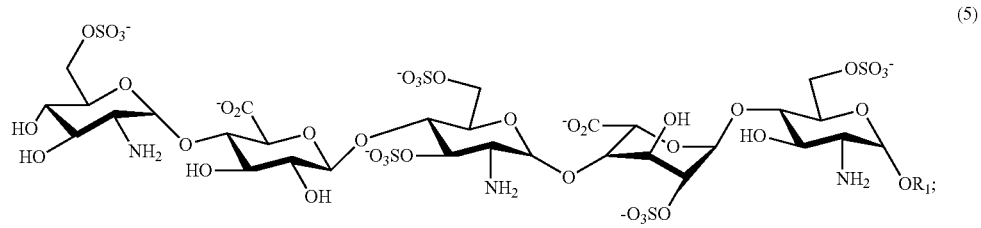

v) reacting the compound of Formula (5) with sulphur trioxide-pyridine complex, giving rise to a compound of formula (6):

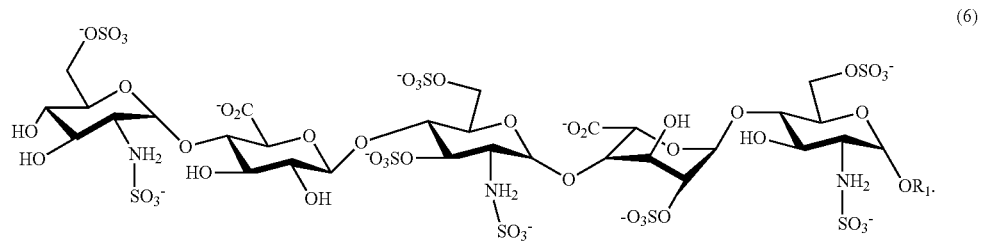

\* \* \* \* \*